United States Patent [19]

Subramanian

[11] Patent Number: 5,242,834
[45] Date of Patent: Sep. 7, 1993

[54] ANALYSIS OF ALUMINUM IN AMINO ACIDS BY HIGH PERFORMANCE LIQUID CHROMATOGRAPHY

[75] Inventor: Durga V. Subramanian, Groton, Mass.

[73] Assignee: Hampshire Chemical Corp., Lexington, Mass.

[21] Appl. No.: 792,124

[22] Filed: Nov. 14, 1991

[51] Int. Cl.⁵ .................. G01N 33/20; G01N 30/02
[52] U.S. Cl. ......................... 436/73; 436/74; 436/161; 436/174; 436/175; 436/182; 73/61.52; 210/656
[58] Field of Search .............. 436/73, 74, 161, 174, 436/175, 182, 86; 210/635, 656; 73/61.52

[56] References Cited

U.S. PATENT DOCUMENTS

| | | | |
|---|---|---|---|
| 4,326,940 | 4/1982 | Eckles et al. | 204/232 |
| 4,364,263 | 12/1982 | Sankoorikal et al. | 73/61.1 |
| 4,737,465 | 4/1988 | Bond et al. | 436/73 |
| 4,871,525 | 10/1989 | Giovanniello et al. | 423/463 |
| 4,943,637 | 7/1990 | Seino et al. | 548/260 |

OTHER PUBLICATIONS

Hoshino et al, "Highly Selective Determination of Trace Metal Ions with 2,2'-DHAB by Ion-Pair Reversed-Phase Partition HPLC-Spectrophotometric Detection System", Chemistry Letters, pp. 1445-1448, 1984.
Karger et al., Reversed-Phase High-Performance Liquid Chromatography Using Metal Chelate Additives, J. Chromatography, v. 167, pp. 253-272, 1968.
Kaneko et al., Ion-Pair Adsorption Film Colorimetry—A New Simple Method for ppb Level of Aluminum Ion in Water Sample, Mikrochimica Acta 1988 vol. 3 pp. 333-340.
Kaneko et al., HPLC-Spectrophotometric Detection Systems for Trace Metal Ions-Fundamentals and Applications, Biomed. Res. Trace. Elem. vol. 1, No. 2, pp. 231-232, 1990.
"Analytical Applications of Gas Chromatography", Allen Ainsworth Duswalt, Jr., 1959, p. 74.
ANALYST, Hoshino et al. Feb. 1990, vol. 115, pp. 133-137.
"On Column Selective Destruction and Separation Mode High-Performance Liquid Chromatography for Ultra-Trace Amounts of Metal Ions", Rep. Asahi Glass Found., Ind. Technoll. 53, 1988, pp. 327-334.
Anal. Chem. 1991 63, 2219-2222.

Primary Examiner—James C. Housel
Assistant Examiner—Jan M. Ludlow
Attorney, Agent, or Firm—Nields & Lemack

[57] ABSTRACT

An analytical method for determining aluminum in amino acids such as glycine. A complex of aluminum and dihydroxyazobenzene is formed by reacting the amino acid solution with a mixture of dihydroxyazobenzene and acetonitrile in the presence of a buffer to obtain a pH of between about 7 and 8. The resulting complex is analyzed for aluminum by high performance liquid chromatography. Minimization of aluminum contamination is achieved by reducing the number of reagents used in the procedure.

5 Claims, 2 Drawing Sheets

|  | A | B | C | D | E | F | G | H | I | J |
|---|---|---|---|---|---|---|---|---|---|---|
| 1. |  |  |  |  |  |  |  |  |  |  |
| 2. |  |  |  |  |  |  |  |  |  |  |
| 3. |  |  | TABLE 1 |  |  |  |  |  |  |  |
| 4. | CENTRIFUGE TUBE # | SAMPLE NAME | BATCH ID | WT. OF SAMPLE, G | ALUMINUM SPIKE, ng | HEIGHT COUNT I | HEIGHT COUNT II | AVERAGE HT. CT. |  |  |
| 5. |  |  |  |  |  |  |  |  |  |  |
| 6. | 1 | WATER | — |  | 0 | 7624 | 7600 | 7612 |  |  |
| 7. | 2 | WATER | — |  | 0 | 7499 | 7649 | 7574 | 0 |  |
| 8. | 3 | GLYCINE | 69 | 1.001 | 0 | 31888 | 32440 | 32164 | 24571 |  |
| 9. | 4 | GLYCINE | 69 | 1.001 | 0 | 27586 | 28033 | 27810 | 20217 | 0 |
| 10. | 5 | GLYCINE | 69 | 1.001 | 50 | 38608 | 38155 | 38382 | 30789 | 10572 |
| 11. | 6 | GLYCINE | 69 | 1.001 | 100 | 47525 | 48349 | 47937 | 40344 | 20127 |
| 12. | 7 | GLYCINE | 69 | 1.001 | 200 | 76770 | 74286 | 75528 | 67935 | 47718 |
| 13. |  |  |  |  |  |  |  |  |  |  |
| 14. | SLOPE | X-INTERCEPT |  |  |  |  |  |  |  |  |
| 15. | 0.0041569 | −78.0 |  |  |  |  |  |  |  |  |

FIG. 2

ANALYSIS OF ALUMINUM IN AMINO ACIDS BY HIGH PERFORMANCE LIQUID CHROMATOGRAPHY

BACKGROUND OF THE INVENTION

The source of amino acids in parenteral nutrition is generally the amino acid in its free crystalline form. Aluminum is a contaminant in amino acids, and therefore, in parenteral solutions. Indeed, the Food and Drug Administration is considering proposing regulations regarding aluminum content of parenteral solutions. Large volume parenterals may need to be certified for an upper limit of aluminum and small volume parenterals may need to be labelled for aluminum content. In addition, environmental and health concerns dictate that even low levels of aluminum may be undesirable.

Accordingly, there exists a need in the industry to easily and effectively quantify the amount of aluminum in amino acids on a parts-per-billion basis. Most methods proposed for aluminum determinations have poor sensitivity at low levels of aluminum. Graphite Furnace Atomic Absorption Spectrometer detection is currently utilized for low level aluminum detection, however, the equipment is expensive and the results obtained often are not reproducible.

The application of high-performance liquid chromatography (HPLC) has been suggested to quantify aluminum levels. Specifically, salicylaldehydebenzoyl-hydrazone (SAB) has been disclosed as an HPLC pre-column derivatizing agent. A resultant highly fluorescent aluminum-SAB chelate is separated on a LiChroCART RP-18 column with an acetonitrile-water eluent containing tetrabutylammonium bromide, disodium EDTA and sodium acetate. In this manner, aluminum ion in water, and reagent alkalihydroxide pellets (LiOH, NaOH and KOH) were determined.

Similarly, 2,2'-dihydroxyazobenzene derivatives have been disclosed as reagents for trace metal determination in coal fly ash by ion-pair reversed-phase high performace liquid chromatography with spectrophotometric detection.

However, the prior art methods involving HPLC can introduce aluminum contamination, which leads to inaccurate results. At the low levels of aluminum involved, even trace amounts of contamination become significant.

It is therefore an object of the present invention to provide an improved method for determining aluminum at the parts per billion level by HPLC. The method is particularly applicable in quantitatively assaying for low levels of aluminum in amino acids in parenteral solutions.

SUMMARY OF THE INVENTION

The problems of the prior art have been overcome by the present invention, which provides an improved analytical method for determining aluminum in amino acids. For purposes of illustration only, glycine will be discussed hereinafter as the amino acid being assayed, although it should be understood by those skilled in the art that the instant invention is applicable to other amino acids commonly used in parental solutions. The method is based upon the reaction of aluminum with dihydroxyazobenzene to produce a complex that can be successfully chromatographed on a reversed phase column using ion pair reagents. A significant aspect of the present invention is the minimization of aluminum contamination by reducing the number of reagents used in the procedure.

BRIEF DESCRIPTION OF THE DRAWINGS

FIG. I is a graphical representation of Time vs. Aluminum-DHAB peak response;

FIG. II is a table of the height count of the HPLC analysis of aluminum; and

Figure 1:
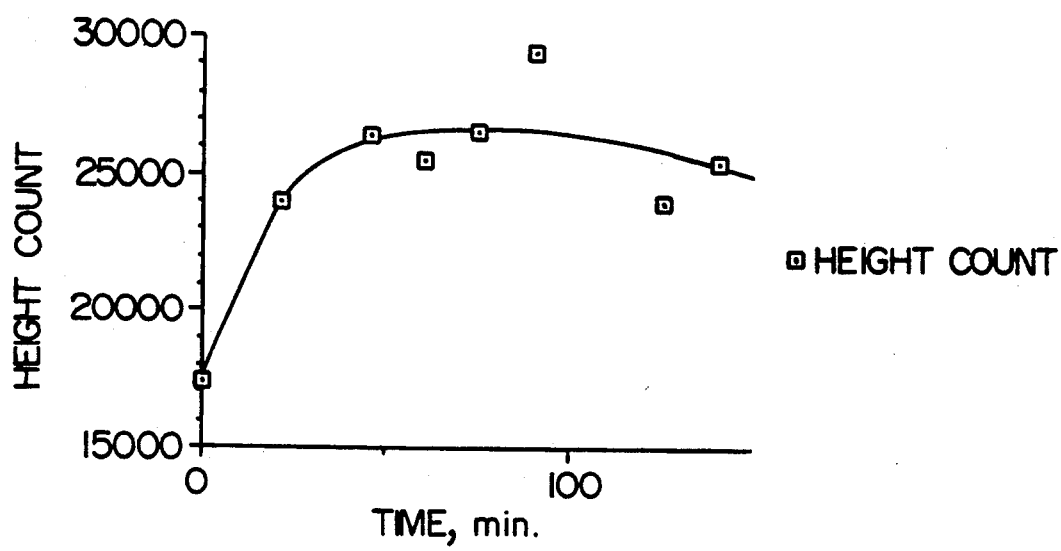
Figure 3:
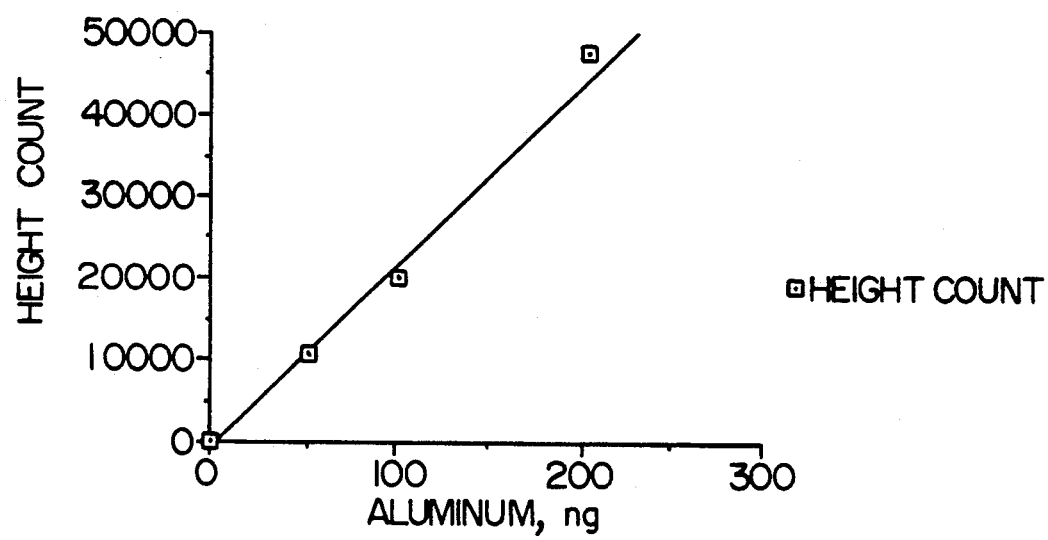

FIG. III is a graphical representation of aluminum (ng) spikes vs. height counts of Aluminum-DHAB peak.

DETAILED DESCRIPTION OF THE INVENTION

Dihydroxyazobenzene (DHAB) complexes with aluminum in 1:1 and 1:2 molar ratios:

$$Al^{+3} + DHAB \rightarrow Al(DHAB)^{+1} + [Al(DHAB)_2]^{-1}$$

The 1:1 complex prevails at lower pH conditions, and the 1:2 complex takes over at higher pH. Preferably, the reaction and chromatography in accordance with the present invention are performed within a pH range so as to minimize the formation of the 1:1 complex. A suitable pH range is from about 7 to about 8, more preferably from about 7.5 to about 7.8.

The DHAB reagent and the $[Al(DHAB)_2]^{-1}$ complex absorb at similar wavelengths. This property makes a direct spectrophotometric determination of the Al-complex unattractive. However, the fact that aluminum and the complex absorb at similar wavelengths is advantageous for their spectrophotometric detection once they have been separated chromatographically. Use of an ion pair reagent such as tetrabutyl ammonium bromide allows the separation of the charged species. Detection at 510 nm yields little background absorbance due to other components of the chromatographic system.

An important parameter in the present procedure is the elimination of aluminum contamination. Common sources of such contamination include the apparatus (especially glassware) involved in the laboratory analysis and the reagents employed in the procedure. Preferably, at the laboratory level, plastic is used instead of glassware where practical. The water used should preferably contain less than about 2 ppb aluminum. Milli-Q ® water available from Millipore has been found to be adequate. "Low level metals" grade acids and bases should be employed.

Tris (hydroxymethyl)aminomethane and morpholine propane sulfonic acid are suitable buffers for the mobile phase, and also can be used to maintain the pH of the aluminum/DHAB reaction in the desired range. Where tris (hydroxymethyl)aminomethane is used, preferably it is cleansed of aluminum contamination by washing with DHAB. By cleaning the buffer with the same reagent used for complexing the aluminum, aluminum contamination can be reduced, since the necessity to use a further, different reagent is eliminated. Similarly, by using the cleaned buffer for pH adjustment of the aluminum/DHAB reaction system, the requirement of similar pH adjustment by using additional acids or bases is eliminated.

A suitable procedure for cleaning the buffer is as follows. The buffer is dissolved in Milli-Q water and the pH adjusted to about 7.5-7.8 with concentrated hydrochloric acid. Separately, DHAB and tetramethylammonium bromide are dissolved in methylene chloride, and the solution is added to the buffer. A two layer mixture is formed, and the aqueous layer containing the buffer is separated. The aluminum forms a complex with the DHAB in the organic layer. The aqueous layer may be treated the same way an additional two times to ensure adequate extraction of aluminum into the organic layer. The resulting buffer has a pH within the desired range of about 7-8. Accordingly, no further adjustment of pH is necessary, thereby eliminating the use of additional acids and bases which may add to contamination.

As the reagent for the aluminum chelation, DHAB dissolved in acetonitrile is suitable. Acetonitrile is commercially available (e.g., VWR Catalog #EM-AX0155-3) with relatively low aluminum levels. By using acetonitrile, aluminum contamination is further minimized by eliminating the necessity of using sodium hydroxide and polyoxy-ethylene nonyl phenol as a nonionic surfactant.

In order to determine the reaction conditions to be employed in forming the $[Al(DHAB)_2]^{-1}$ complex, the following test was carried out.

TEST EXAMPLE 1

10 grams of glycine were dissolved in water to make 50 ml. of solution. 5 ml. aliquots were placed in several centrifuge tubes. Tris (hydroxymethyl)aminomethane buffer was added to the 15 ml. mark followed by 5 ml. of DHAB in acetonitrile. The centrifuge tubes were swirled to ensure mixing of the layers, covered and placed in a water bath maintained at 85°-90° C. The test tubes were removed at different intervals of time, and volumes made up to 20 ml. with acetonitrile. Plastic WISP vials were filled with these solutions and analyzed using the following chromatographic conditions:

| | |
|---|---|
| Mobile Phase Flow | 2 ml/min. (The system was equilibrated for at least one hour. The mobile phase was recirculated after equilibration). |
| Injection Volume | 200 μl |
| Run Time | 21 minutes |
| Number of Injections/vial | 2 |
| Detection wavelength | 510 nm |
| AUFS setting | 0.04 |
| Chart speed | 0.5 cm/min |

The height counts of the Al-DHAB peak were plotted versus time of incubation. The results are shown in FIG. I. The profile demonstrates that the reaction does not go to completion instantaneously. Preferably, the reactants are heated for about 45 to about 60 minutes, preferably about 60 minutes. The temperature to which the reactants are heated is about 85°-90° C., preferably about 90° C.

EXAMPLE 1

Aluminum Standard Preparation 100, 10, 1 and 0.1 ppm standards were prepared as follows:

100 ppm standard: 5 ml. of Aluminum AA (1000 ppm) standard were pipetted into a 50 ml. volumetric flask. Sufficient water (Milli-Q) was added to make a 50 ml. solution.

10 ppm standard: 5 ml. of the 100 ppm standard was pipetted into a 50 ml. volumetric flask and brought to volume with water.

1 ppm standard: 5 ml. of the 10 ppm standard was pipetted into a 50 ml. volumetric flask and brought to volume with water.

0.1 ppm standard: 10 ml. of the 1 ppm standard was pipetted into a 100 ml. volumetric flask and brought to volume with water.

Mobile Phase Preparation 600 ml. of methanol and 400 ml. of Milli-Q water were combined in a 1000 ml. Nalgene flask. A clean magnetic stir bar was placed in the flask and the following were added to the methanol-water solution while stirring:

600 mg of tetrabutyl ammonium bromide
30 mg of EDTA acid
250 mg of purified TRIS.HCl The pH of the resulting solution was in the range of 7.5-7.8; no further pH adjustment was necessary.

Reagent Preparation for Aluminum Chelation

Buffer: 1.7 grams of purified tris(hydropymethyl)aminomethane. HCl(TA.HCl) was dissolved in 250 ml. of water.

DHAB: 12 mg. of DHAB was dissolved in 200 ml. of acetonitrile.

Procedure

10+/−0.01 grams of glycine sample was weighed into a 50 ml. volumetric flask. Water was added to bring the total volume to about 45 ml. The flask was covered and sonicated for 10 minutes. The flask was then placed in an 80° C. water bath to facilitate the dissolution of the glycine. After the sample had dissolved completely, the sample was brought to volume with water. 5 ml. of water was pipetted into each of two centrifuge tubes. 5 ml. of the glycine sample was pipetted into each of 5 sample centrifuge tubes. Into three of the sample centrifuge tubes was added 0.5, 1.0 and 2 mls. of 0.1 ppm aluminum standard, respectively. Sufficient buffer was then added to each of the seven tubes to bring the volume to 15 ml. The tubes were then brought to 20 ml. with the DHAB reagent solution, were mixed by swirling and were covered.

The tubes were placed upright in a beaker. Hot water was added to the beaker to the level of the liquid in the tubes. The beaker was placed in a Milli-Q water bath so that the reaction solutions were maintained at 85°-90° C. for 60 minutes, and the tubes were removed and allowed to cool. Where evaporation occurred, sufficient acetonitrile was added to return the volume to 20 ml, and the samples were mixed by swirling.

Plastic WISP vials were filled with the reaction solutions, and were capped with screw caps and liners. The solutions were analyzed by HPLC using the same instrument conditions as in Test Example 1. Under these conditions, the unused reagent elutes at about 12 minutes and the aluminum-DHAB complex elutes at about 4-6 minutes. The height counts of the peaks are tabulated in FIG. II. The aluminum content is illustrated graphically in FIG. III.

What is claimed is:

1. A method of determining aluminum content of a solution comprising an amino acid, comprising:
   a. forming a complex of aluminum and dihydroxyazobenzene by reacting said solution with a mixture of dihyroxyazobenzene and acetonitrile in the presence of sufficient buffer to obtain a pH between about 7 and 8, and at a temperature of about 85°-90° C.;
   b. analyzing the resulting complex for aluminum by high performance liquid chromatography; and c. calculating the amount of aluminum present.

2. The method of claim 1 wherein the reaction in step a is carried out for about 45–60 minutes.

3. The method of claim 1 wherein said amino acid is glycine.

4. The method according to claim 1 wherein said buffer is tris(hydroxymethyl)aminomethane.

5. The method according to claim 4 wherein aluminum is removed from said tris(hydroxymethyl)aminomethane by contacting said tris(hydroxymethyl)aminomethane with an immiscible solution of dihydroxyazobenzene, tetramethylammonium bromide and methylene chloride.

* * * * *